United States Patent [19]
Andreiko et al.

[11] Patent Number: 5,622,494
[45] Date of Patent: Apr. 22, 1997

[54] PLASTIC ORTHODONTIC APPLIANCE HAVING A MECHANICAL BONDING BASE AND METHOD OF MAKING SAME

[75] Inventors: Craig A. Andreiko, Alto Loma; David L. Ludwig, San Juan Capistrano, both of Calif.

[73] Assignee: Ormco Corporation, Glendora, Calif.

[21] Appl. No.: 391,663

[22] Filed: Feb. 21, 1995

[51] Int. Cl.⁶ ...................................................... A61C 7/14
[52] U.S. Cl. .......................................................... 433/9
[58] Field of Search ............................................ 433/8, 9

[56] References Cited

U.S. PATENT DOCUMENTS

| | | | |
|---|---|---|---|
| D. 290,040 | 5/1987 | Kelly | D24/16 |
| D. 340,523 | 10/1993 | Barngrover . | |
| 3,765,091 | 10/1973 | Northcutt | 32/14 A |
| 3,930,311 | 1/1976 | Andrews | 32/14 A |
| 3,975,824 | 8/1976 | Lee | 32/14 A |
| 4,068,379 | 1/1978 | Miller et al. | 32/14 A |
| 4,100,678 | 7/1978 | Yatabe | 32/14 A |
| 4,165,561 | 8/1979 | Miller et al. | 32/14 A |
| 4,243,386 | 1/1981 | Kawaguchi | 433/9 |
| 4,299,569 | 11/1981 | Frantz | 433/8 |
| 4,322,206 | 3/1982 | Reynolds | 433/9 |
| 4,369,033 | 1/1983 | Webb et al. | 433/9 |
| 4,430,061 | 2/1984 | Webb et al. | 433/9 |
| 4,460,336 | 7/1984 | Smith et al. | 433/9 |
| 4,479,527 | 10/1984 | Boettcher | 164/34 |
| 4,531,566 | 7/1985 | Boettcher | 164/246 |
| 4,544,353 | 10/1985 | Maurer et al. | 433/9 |
| 4,604,057 | 8/1986 | Viglietti | 433/9 |
| 4,626,209 | 12/1986 | Tsai et al. | 433/9 |
| 4,661,059 | 4/1987 | Kanno . | |
| 4,681,538 | 7/1987 | DeLuca et al. | 433/9 |
| 4,698,017 | 10/1987 | Hanson | 433/11 |
| 4,752,221 | 6/1988 | Hanson et al. | 433/9 |
| 4,838,786 | 6/1989 | Reher et al. | 433/9 |
| 4,842,513 | 6/1989 | Haarmann | 433/9 |
| 4,927,361 | 5/1990 | Smith et al. | 433/9 |
| 4,936,773 | 6/1990 | Kawaguchi | 433/9 |
| 5,071,344 | 12/1991 | Wong et al. | 433/8 |
| 5,078,596 | 1/1992 | Carberry | 433/9 |
| 5,095,602 | 3/1992 | Reher et al. | 29/160.6 |
| 5,108,285 | 4/1992 | Tuneberg | 433/9 |
| 5,154,606 | 10/1992 | Wildman | 433/8 |
| 5,158,452 | 10/1992 | Franseen et al. | 433/9 |
| 5,252,066 | 10/1993 | Fairhurst | 433/9 |
| 5,254,003 | 10/1993 | Andreiko . | 433/9 |
| 5,267,854 | 12/1993 | Schmitt . | |
| 5,295,823 | 3/1994 | Farzin-Nia | 433/9 |
| 5,522,725 | 6/1996 | Jordan et al. | 433/9 |

FOREIGN PATENT DOCUMENTS 2563426  10/1985  France .

Primary Examiner—Paul J. Hirsch
Attorney, Agent, or Firm—Wood, Herron & Evans

[57] ABSTRACT

This invention is directed to a plastic orthodontic appliance having projecting structure extending outwardly from a bonding base. The projecting structure includes a broadened outer extremity and undercuts proximate the outer extremity which form mechanical bonds with a bonding adhesive. In one application, a plurality of appliances in the form of slotted brackets is provided for cooperating with an archwire to apply corrective forces to a patient's teeth on which the brackets are mounted. Another aspect of the invention concerns a method of making plastic orthodontic appliances suitable for mechanical bonding. The method includes molding a plastic orthodontic appliance having undeformed projecting structure and subsequently softening and compressing the outer extremity of the projecting structure to form undercuts. In a preferred embodiment, the projecting structure is a plurality of posts.

16 Claims, 4 Drawing Sheets

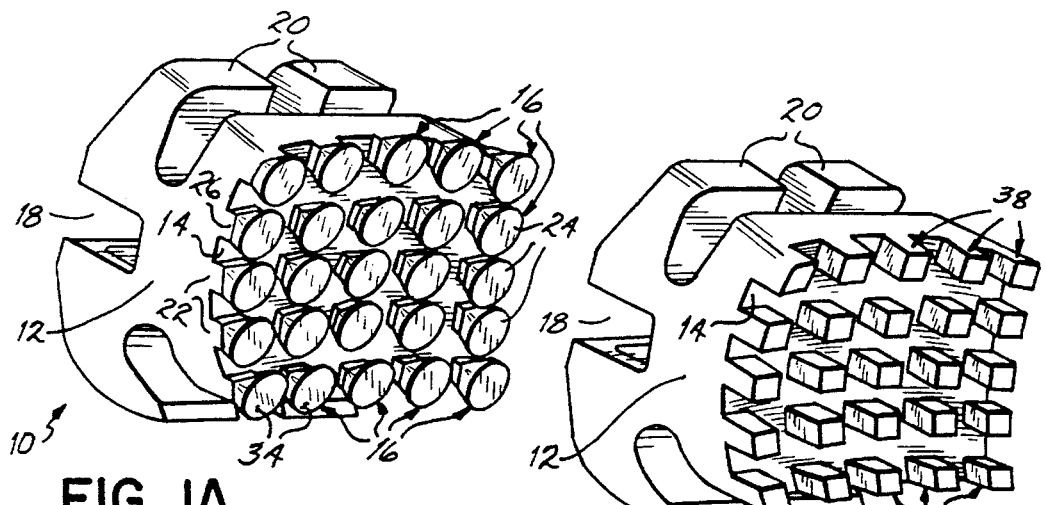
FIG. 1A
FIG. 1B
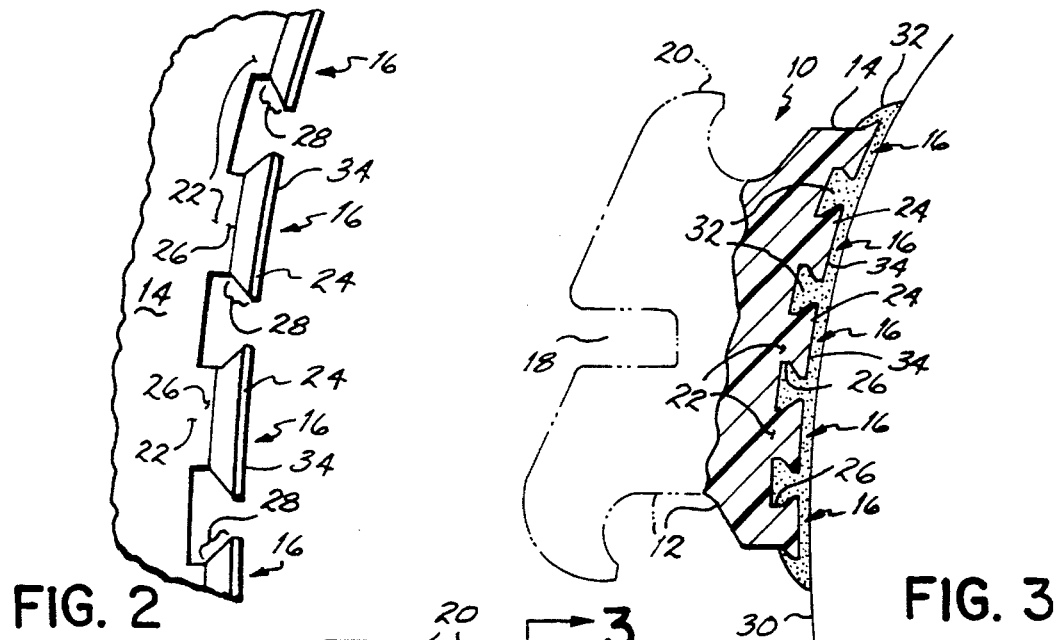
FIG. 2
FIG. 3
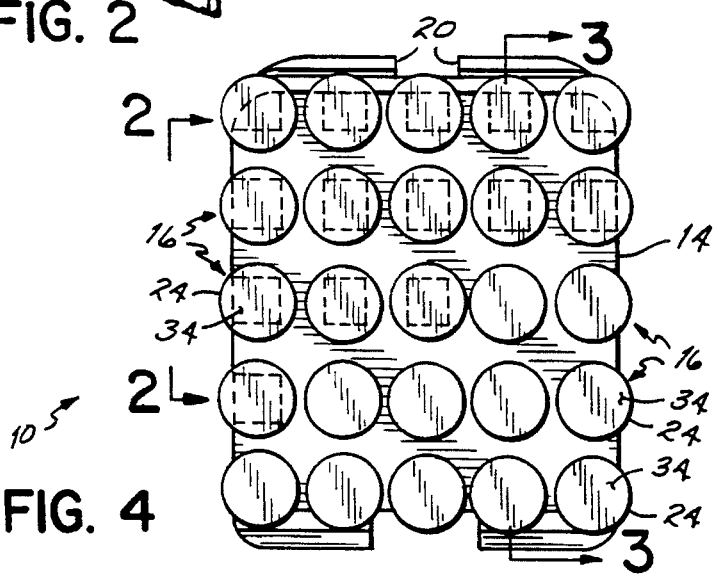
FIG. 4

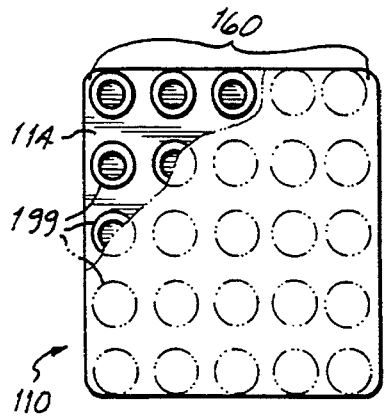 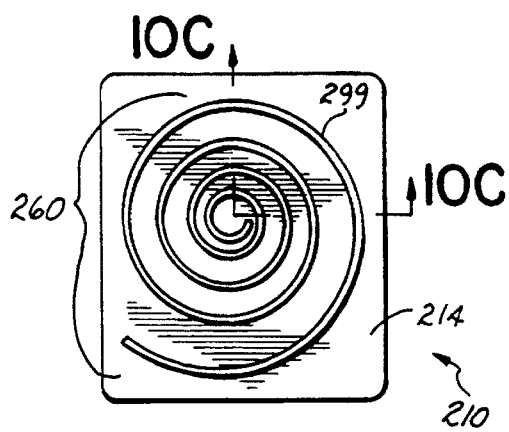
FIG. 10A　　　　　　　FIG. 10B
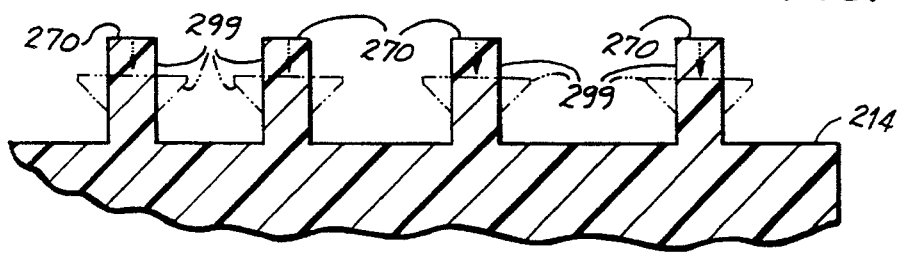
FIG. 10C
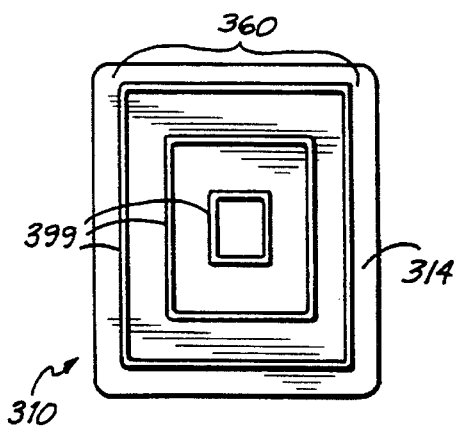 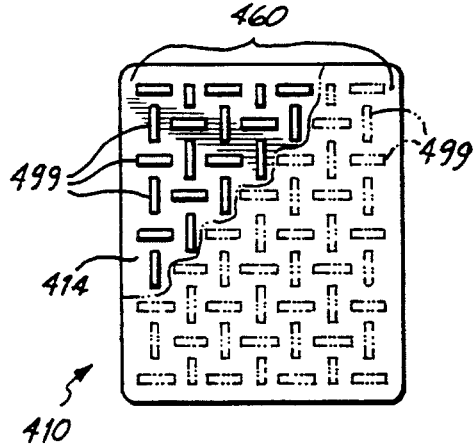
FIG. 10D　　　　　　　FIG. 10E
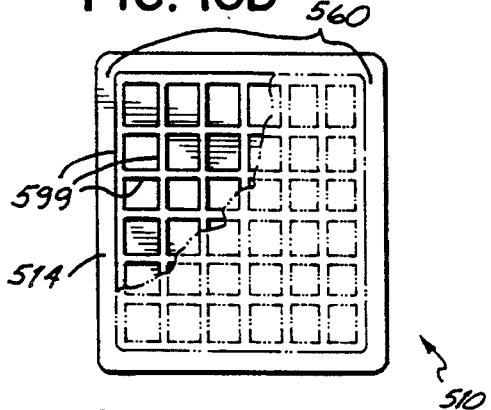
FIG. 10F

PLASTIC ORTHODONTIC APPLIANCE HAVING A MECHANICAL BONDING BASE AND METHOD OF MAKING SAME

FIELD OF THE INVENTION

This invention is directed to orthodontic appliances, and more particularly, to a plastic orthodontic appliance having projecting structure extending outwardly from an appliance base, preferably either a plurality of discrete projections, posts or ridges or a single elongated continuous projection or ridge, which incorporates undercuts at its outer extremity to mechanically bond the appliance to a tooth surface with an adhesive.

BACKGROUND OF THE INVENTION

In the field of orthodontics, it is known to adhere orthodontic appliances, such as brackets, buccal tubes and the like, directly to teeth. Typically, this is accomplished by chemically bonding an appliance to a tooth surface using an adhesive. If desired, the bonding surface area of the appliance may be roughened in order to increase the surface area of the appliance in contact with the adhesive, thereby enhancing the chemical bond. Direct bonding also may be accomplished by using a metal appliance having undercuts for forming a mechanical bond with the adhesive.

U.S. Pat. No. 5,267,854 to Schmitt teaches a metal injection molded orthodontic bracket including a plurality of raised posts buccolingually extending from a tooth abutting surface. Each post includes a root section having a base integrally formed with the tooth abutting surface and an apex section buccolingually extending from the root section. The apex section terminates in a sharp, continuous parameter edge that was originally smaller in all directions than the root section. However, in accordance with the invention, further cold working of the parameter edges occurs whereby each edge is worked at ambient temperatures into a mushroom-shaped button having a worked edge larger in all directions than its associated root section and an eave capable of mechanically bonding with an adhesive.

U.S. Pat. No. 4,661,059 to Kanno features a metal orthodontic bracket which has a base surface provided with a plurality of orthogonal grooves formed by a cutting machine having a plurality of rotatable thin circular cutter blades. The grooves have small fins or flashes at the edges of the grooves resulting from cutting operations of cutter blades scraping metal matrix at high speed. These small fins are pressed down into the inside of the grooves to form undercuts for the adhesive to provide mechanical bonding of the base to the tooth surface.

Although mechanical bonding provides some advantages over traditional bonding methods, the brackets taught by Schmitt and Kanno have several limitations. For example, both brackets are made of metal, and therefore lack the aesthetic qualities found in plastic or ceramic orthodontic appliances. Furthermore, the mechanical bonding surfaces of the Schmitt and Kanno brackets are formed by cold working the metal at ambient temperature. This cold working process also distorts the microstructure of the raised posts used for mechanical bonding.

In addition, the methods used to form the mechanical bonding surfaces are relatively complex and expensive. The Schmitt patent requires the use of a hydraulically activated metal working die to cold work the posts, while Kanno teaches the use of a cutting machine to form the posts in the bracket base, which leads to a significant amount of wasted metal. Also, the raised posts of the Schmitt bracket must be originally molded with an apex section narrower than the root section, in order to remove the metallic bracket from the mold without significant risk of peg breakage. This tapering results in less metal being available at the apex to form the mushroom-shaped button and corresponding eave required for mechanical bonding. Furthermore, the extremely fine fins or flashes of the Kanno bracket formed by the cutting process must be pressed downward in order to form the mechanical bonding surfaces, and are subject to stress and fracture in this process.

Therefore, it would be beneficial to have an orthodontic appliance capable of being mechanically bonded to a tooth, in which the appliance is made of an aesthetically pleasing material. It also would be desirable to have a method for forming such an appliance which is relatively simple and inexpensive and which does not compromise the strength of the material.

SUMMARY OF THE INVENTION

This invention is directed to a process for forming an orthodontic appliance, and the appliance so formed, having projecting structure extending from an appliance base which is adapted to mechanically bond to a tooth surface with an adhesive. The process includes injection molding a thermoplastic orthodontic appliance having a base from which outwardly extends a projecting structure, such as a ridge, posts or the like. The projecting structure has an inner extremity and an outer extremity, with the inner extremity being integrally connected to the appliance base. The process further includes softening the outer extremity, which may be a plurality of discrete outer ends if posts are used, and applying pressure thereto while in a softened state so as to deform the projecting structure and provide undercuts proximate the outer extremity for facilitating mechanical bonding of the appliance base to a tooth surface.

The softening step may be accomplished by transferring energy, such as heat or ultrasonic energy, to the outer extremity of the projecting structure. If heat transfer is used, heat may be transferred conductively to the outer extremity of the projecting structure by contacting the outer extremity with an external heat source such as a heating element or the like. In order to soften the projecting structure, the heating element should have a temperature above the glass transition temperature of the plastic. The thermoplastic orthodontic appliance typically is formed of a glass-filled polycarbonate material, in which case the heating element preferably has a temperature of from about 350° F. to about 400° F., more preferably about 390° F.

In a preferred form of the process, the heating element has a substantially continuous smooth surface such that the same heating element may be used during the softening step regardless of the exact location of the projecting structure relative to the curved appliance base, minimizing alignment problems. Furthermore, a preferred heating element has a size and curvature such that, when the orthodontic appliance employs a plurality of discrete projections, the heating element contacts the outer ends of the projections substantially simultaneously, with the configuration of the curvature of the heating element matching that of the tooth surface to which the appliance base is to be mounted.

The pressure application step generally includes applying pressure to the outer extremity of the projecting structure in a direction along the length thereof toward the base, thereby slightly compressing the projecting structure. This pressure application step deforms the softened outer extremity of the projecting structure into a substantially mushroom-shaped configuration to thereby provide the undercuts proximate the outer extremity. In a preferred form of the invention, when the orthodontic appliance employs a plurality of projections, the pressure application step includes applying pressure substantially simultaneously to the outer ends of all of the projections. Preferably, the projecting structure is compressed in the range of about 0.001 inch to about 0.004 inch in length. In the preferred embodiment, the pressure is applied to the outer extremity of the projecting structure using a heating element, in which case the heat transfer step and pressure applying step temporally overlap.

The projecting structure itself may be one, or several, of many different shapes and alignments extending from the appliance. For example, a solid post or posts, a hollow tubular post or posts, a bristle or bristles, a ridge or ridges, or combinations thereof, may be used. If a plurality of posts is used, preferably, each of the posts has a generally square shaped cross-sectional area along its entire length prior to deformation of the outer ends thereof. A cross-sectional dimension of about 0.015 inch by about 0.015 inch is preferable. In the preferred embodiment, the posts are located on an imaginary grid and are spaced such that the center-to-center distance from one post center to an adjacent post center is approximately 0.030 inch. Furthermore, the posts have a length of from about 0.005 inch to about 0.010 inch.

When the orthodontic appliance is formed as an orthodontic bracket, the plastic may include reinforcing glass fibers and may have a reinforcing insert proximate an archwire slot.

Another aspect of the invention concerns providing a plurality of orthodontic appliances, such as brackets, mechanically bonded to the teeth using an adhesive, with an archwire disposed within the archwire slots of the brackets for transferring forces to the teeth.

The inventive orthodontic appliance and method discussed above offer several benefits and advantages. For example, the appliance offers the strength of a mechanical bonding surface, as well as increased surface area for chemical bonding, in an aesthetically pleasing orthodontic appliance. Whereas conventional mechanical bonding brackets are formed of a metal such as stainless steel, the inventive appliance is formed of an aesthetically pleasing thermoplastic such as polycarbonate, which typically has a translucent tooth-like appearance. Furthermore, the method for forming the appliance is relatively simple and inexpensive in comparison with the cold working methods presently used on metal brackets. Also, the cold working distorts the microstructure of the raised metal posts, whereas the plastic softening and pressure applying steps of the invention form undercuts in the thermoplastic posts without distorting the microstructure thereby maintaining the structural integrity of the plastic material.

In addition, the plastic orthodontic appliance of this invention is compatible with typical orthodontic adhesives and does not require the use of a primer, thereby simplifying the bonding process. Because many traditional, smooth bonding base plastic brackets require a primer before an adhesive may be applied, an orthodontist usually must perform this additional step chairside. Furthermore, with prior art plastic brackets, the adhesive used must be able to form a chemical bond with the primer and bracket, thereby limiting the kinds of orthodontic adhesives which can be used. Because the inventive plastic appliance utilizes mechanical bonding, these problems are avoided.

BRIEF DESCRIPTION OF THE DRAWINGS

FIG. 1A is a rear perspective view of an orthodontic bracket after the posts have been deformed to provide a mechanical bonding base;

FIG. 1B is a rear perspective view of an orthodontic bracket before the posts have been deformed;

FIG. 2 is an enlarged view of the deformed posts of the orthodontic bracket of FIG. 4 taken along line 2—2;

FIG. 3 is a partial cross section of FIG. 4 taken along line 3—3, showing the bracket adhered to a tooth surface;

FIG. 4 is a rear view of the orthodontic bracket of FIG. 1A;

FIGS. 10A, 10B and 10D–10F are rear views of orthodontic appliances, illustrating a few alternate embodiments of the projecting structure in an undeformed state; and FIG. 10C is a partial cross-section of FIG. 10B taken along line 10B—10B, illustrating the projecting structure in both undeformed and deformed (shown in phantom) states.

DETAILED DESCRIPTION OF THE INVENTION

Figure 5:
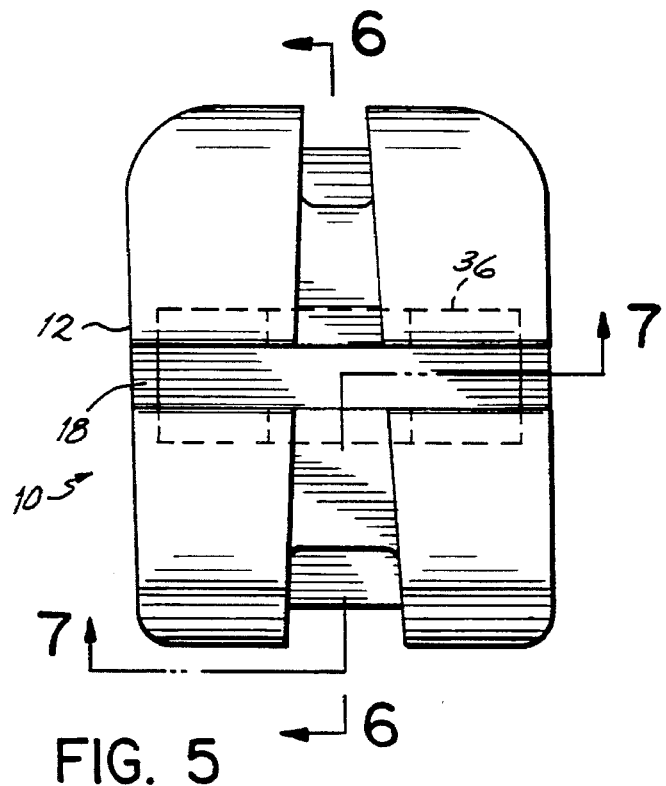
FIG. 5 is a front view of the orthodontic bracket of FIG. 1B.

As used herein, the term "orthodontic appliance" refers to any device which is adhered to a tooth surface in conjunction with moving teeth or holding teeth in a particular position. Non-limiting examples include orthodontic brackets, buccal tubes and the like.[1] In addition, the term "projecting structure" refers to any structure which extends outwardly from an orthodontic appliance base and which may be deformed at its outer extremity, thereby forming an undercut proximate the outer extremity which is adapted to form a mechanical bond with an orthodontic adhesive when the adhesive cures. Nonlimiting examples of projecting structure include a solid post or posts, a hollow tubular post or posts, a bristle or bristles, a ridge or ridges, or a combinations thereof. A few more detailed examples include ridges in the form of concentric circles, squares, triangles or rectangles; solid posts or hollow tubular posts or projections in the form of circles, rectangles or triangles; a nonintersecting single continuous ridge such as a spiral or serpentine zig-zag; plural nonintersecting ridges such as a basketweave pattern, or parallel or randomly aligned ridges; plural or intersecting ridges which intersect to form a grid-like pattern, maze or random orientation; and brush-like bristles.

Referring to FIG. 1 A, a plastic orthodontic bracket 10 according to the principles of the invention includes a body 12 and a bracket base 14, with a plurality of posts 16 extending outwardly from the bracket base 14 in a grid-like pattern. The bracket further includes an archwire slot 18 and a pair of tiewings 20.

As shown in FIG. 2, each of the posts 16 has an inner end 22 integral with the bracket base 14, an outer end 24 and an intermediate section 26 disposed between the inner and outer ends 22, 24. Each post further includes an undercut 28 for forming a mechanical bond with an orthodontic adhesive. Referring to FIG. 3, an orthodontic bracket 10 is shown bonded to a tooth surface 30 using an orthodontic bonding adhesive 32. Typically, an orthodontist will apply the adhesive 32 to the bracket base 14, allowing the adhesive to flow into and fill the open spaces between the posts 16 as well as cover the outer ends 24. The bracket 10 then may be placed on the tooth surface 30, and as the adhesive 32 cures, a chemical bond and a mechanical interlocking bond is formed between the adhesive 32 and the bracket 10 or other orthodontic appliance. A bond is also formed between the adhesive and the tooth surface. The mechanical undercuts 28 in the bracket cause the bracket 10 to more tightly bond to the tooth than a bracket having a smooth bonding surface, thereby enhancing the adhesion of the bracket 10 to a tooth 30. Additionally, the posts 16 increase the surface area of the base 14, enhancing the chemical bonding with the adhesive to the base. Furthermore, it is believed that the bond may be not only similar in strength (shear or tensile force to bond failure at low strain rates) to mesh-based brackets, but also tougher (more impact resistant) than the bond for metal or ceramic brackets, because of the relative flexibility of the posts 16 and the inherent ductility of the plastic material.

Figure 6:
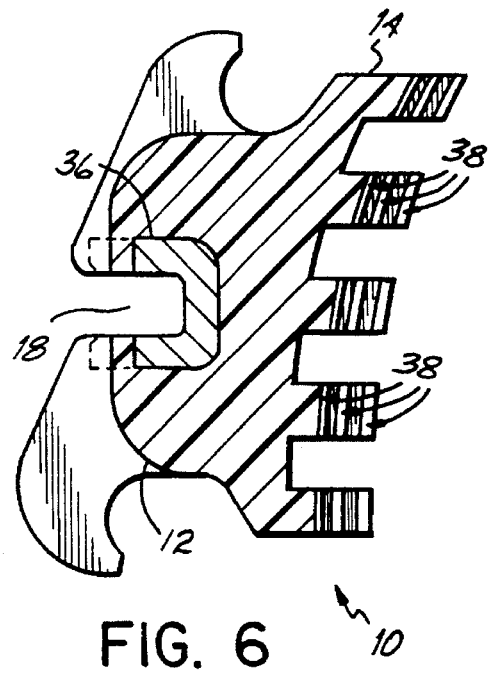
FIG. 6 is a cross-section of the bracket of FIG. 5 taken along line 6—6.
Figure 7:
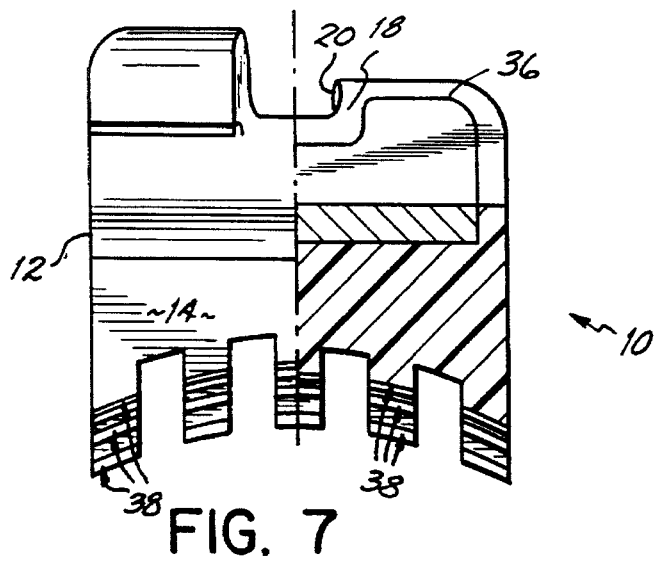
FIG. 7 is a partial cross-section bottom view of the bracket of FIG. 5 taken along line 7—7.

Preferably, the plastic orthodontic appliance is formed of a polycarbonate reinforced with glass fibers as taught in U.S. Pat. No, 5,254,002, which is incorporated in its entirety by reference, with the fibers preferably being about 20%–40% by weight. Referring to FIGS. 6 and 7, when the orthodontic appliance is a bracket 10, the bracket 10 preferably includes a metal insert 36 disposed within the archwire slot 18, as taught in the referenced patent.

The preferred embodiment of the orthodontic appliance also has an appliance base with a compound curvature corresponding to the curvature of a tooth surface. Furthermore, as shown in FIGS. 1A, 1B, 3, 6 and 7, the outer ends 24 of the posts 16, when viewed in combination, generally follow this same compound curvature, both before and after deformation.

As shown in FIG. 4, a preferred embodiment of the appliance has about 25 posts 16 arranged in a grid-like pattern. Each post has a square shaped cross-sectional area through its inner end 22 and intermediate section 26, with dimensions of about 0.015 inch×0.015 in. In addition, referring to FIG. 2, each broadened outer end 24 has a length of about 0.005 in. to about 0.010 in. from the inner end 22 to the tooth facing surface 34 of the broadened outer end 24. As further seen in FIG. 4, the spacing between post inner ends 22 is similar to the cross-sectional dimensions of the inner ends 22 themselves, ranging from about 0.010 in. to about 0.020 in.

Regardless of the particular projecting structure employed, the space between adjacent portions of the deformed outer extremity of the projecting structure (for example, between adjacent broadened outer ends of an embodiment using discrete posts) must be sufficient to permit the adhesive to flow between the deformed adjacent portions into the undercut region below, which is a function of the adhesive viscosity and the method of application of the adhesive to the base.

In another embodiment (not shown) the appliance base has a centrally located area which is free of posts. This open area may be formed with an identifying mark, such as a letter or number, to assist in the identification of the appliance. The portions of the appliance base immediately adjacent to the open area may have partial posts, such as posts with smaller cross-sectional dimensions. While this embodiment slightly reduces the number of posts available for mechanical bonding, it still is able to form a strong mechanical interlock with an adhesive.

Typically, the orthodontic appliance is formed in a multi-step process. As shown best in FIG. 1B, as well as in FIGS. 6 and 7, a preferred bracket 10 or other appliance is molded having undeformed posts 38, and the broadened outer ends of the posts are formed in a secondary operation. The intermediate-stage appliance (having undeformed posts or other projecting structure) may be formed using a conventional thermoplastic molding technique as is taught by U.S. Pat. No. 5,254,002, preferably by injection molding.

Different molds may be used to achieve the desired sizing and distribution of undeformed posts or other projecting structure, and when an appliance having a plurality of posts is to be formed, preferably the mold is shaped so as to produce an appliance having post size and distribution as discussed above. Furthermore, the portion of the appliance mold used to make the undeformed posts or other projecting structure preferably has no draft (i.e., the walls of the cavities in the mold corresponding to the posts may be vertical as opposed to being tapered). This ability to have vertical walls in the mold generally is not possible for a metal bracket having mechanical bonding posts because the greenware (molded metal bracket before sintering) is very fragile, and without tapered side walls in the mold that produce posts which have smaller cross-sectional dimensions toward their outer ends, some posts likely would break as the metal bracket is removed from the mold cavity. However, because the appliances of the present invention are formed of plastic, a mold having vertical side walls may be used without significant risk of projecting structure breakage. This feature provides enhanced strength to the posts or other projecting structure during both initial formation and subsequent broadening of the outer extremity. The feature also produces projecting structure having more material at its outer extremity relative to molded metal posts, thereby enhancing the undercuts and mechanical bonding between the undercuts and the bonding adhesive.

While a preferred embodiment has been described in detail in the form of an orthodontic appliance having a projecting structure comprising a plurality of discrete posts, numerous alternative embodiments of the projecting structure may be provided, a few examples of which are shown in FIGS. 10A–10F.

Referring to FIG. 10A, the orthodontic appliance 110 may have projecting structure 160 extending outwardly from the appliance base 114 which is a plurality of discrete, circular, hollow tubular posts or projections 199. FIG. 10B illustrates an appliance 210 having a projecting structure 260 in the form of a spiral-like ridge 299 extending from the appliance base 214. FIG. 10C is a partial cross-section of the spiral-like ridge 299 of FIG. 10B illustrating the projecting structure 260 in an undeformed and deformed (shown in phantom) state. The outer extremity 270 of the projecting structure 260 also is clearly visible. In FIG. 10D, the appliance 310 has a projecting structure 360 which is a series of concentric rectangles 399 extending outwardly from the appliance base 314, while in FIG. 10E the appliance 410 has a series of discrete nonintersecting ridges 499 aligned in a basket-weave pattern which extend outward from the appliance base 414. The appliance 510 shown in FIG. 10F includes a projecting structure 560 which is a series of intersecting ridges 599 arranged in a grid-like pattern and extending outwardly from the appliance base 514.

Figure 9:
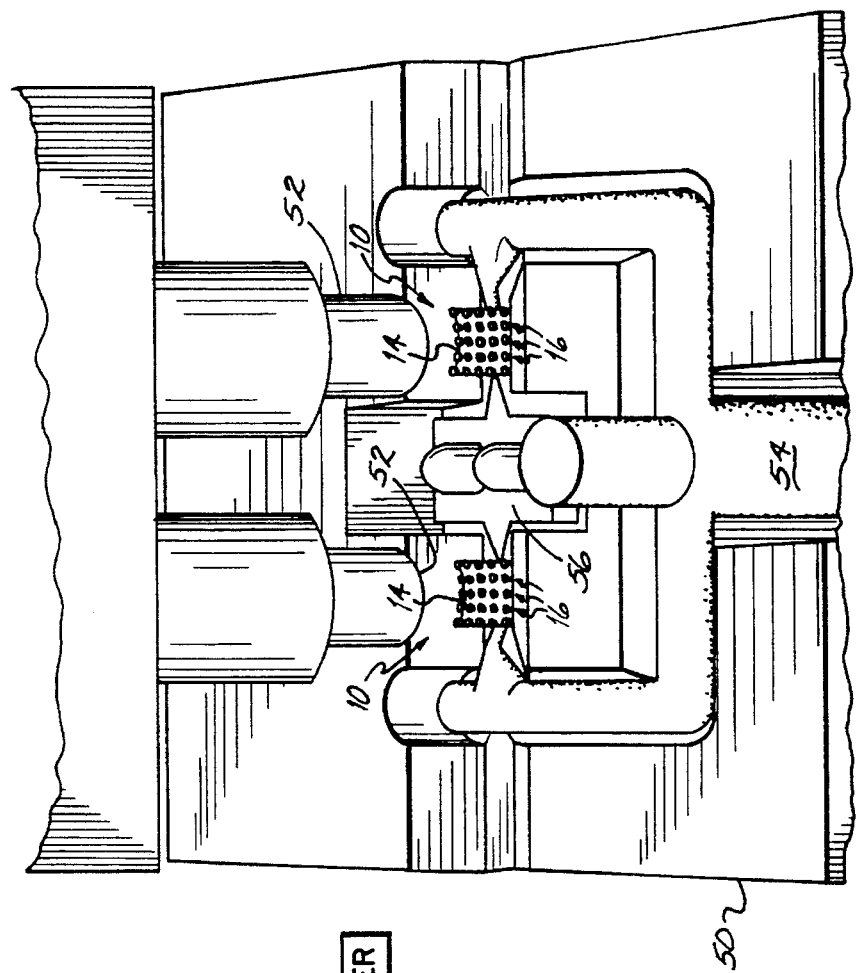
FIG. 9 is a closeup perspective view of the die of the projecting-structure deforming station shown in FIG. 8.
Figure 8:
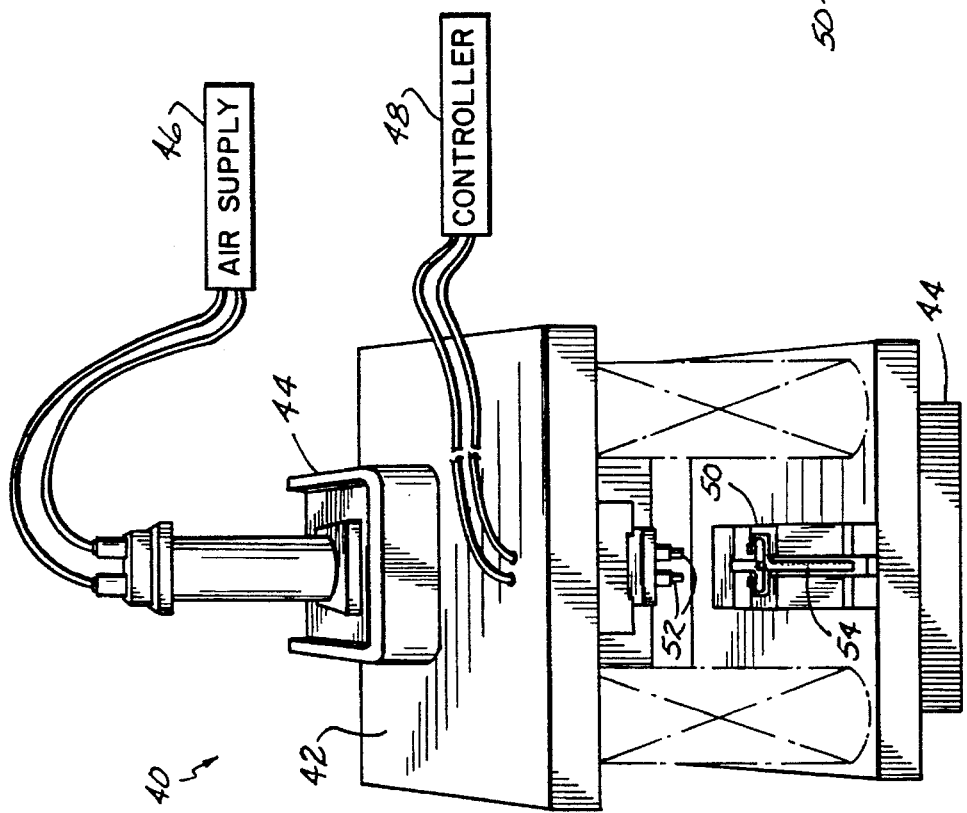
FIG. 8 is a perspective view of a projecting-structure deforming station used in a method of forming an orthodontic appliance.

In the preferred method of forming the orthodontic appliance, the posts or other projecting structure are deformed using a projecting-structure deforming station, a bench-scale version of which is shown in FIGS. 8 and 9. The post deforming station 40 broadly includes a die 42, arbor press 44, air supply 46 and controller 48 as shown in FIG. 8. More specifically, the die includes a holding fixture 50 for holding and positioning an orthodontic appliance or appliances, and a projecting-structure deforming tool 52 positioned directly above each appliance as shown in FIG. 9. Because the deforming tool 52 has a continuous smooth surface, it may be used with appliances having different projecting structure location or density relative to the appliance base. The deforming tool, because it is a single continuous smooth surface rather than a plurality of discrete tools corresponding in number and location to the appliance posts, ridges, bristles, or other projecting structure, does not require critical positioning to precisely align plural tools with plural posts, ridges or the like. Furthermore, each deforming tool 52 has a compound curvature corresponding to the compound curvature of the tooth surfaces to which the appliance is to be mounted. Thus, the contour of the deformed extremity of the projecting structure matches the contour of the tooth surface. In the preferred projecting-structure deforming method, the deforming tips are heated to a temperature which is high enough to bring the outer extremity of the projecting structure to its plastic softening point. When the orthodontic appliance is made of a glass fiber-reinforced polycarbonate, the deforming tool temperature preferably ranges from about 350° F. to about 400° F., more preferably about 390° F.

In the preferred method of forming the appliance, each heated deforming tool 52 moves downward in a substantially smooth and uniform motion toward the projecting structure of the corresponding appliance, and a compressing force is applied to the projecting structure using the deforming tool 52. The projecting structure is softened almost instantly when it is contacted by the tool 52, and the tool 52 continues to advance in a downward compressing direction until it hits a positive hard stop (not shown). Once the deforming tool 52 reaches this hard stop, return springs bias the tool 52 upward to its original position. Typically, the force needed to move the heated deforming tool 52 downward is only slightly in excess of the force needed to overcome the bias on the return springs.

The deformed posts 16 then are allowed to cool and harden, and any sprue 54 is trimmed from each appliance. If the appliance is formed with a reinforcing insert, such as a ceramic or a metal insert, the main handling section 56 of the metal insert as shown in FIG. 9 may be trimmed from the appliance. Although thermal energy preferably is used to soften the undeformed posts, the posts may be softened using a number of other methods, such as ultrasonic energy, microwave energy and the like. Thermal energy is preferred, however, because it has been found to be easier to control the amount of deformation and the shape of the posts using this energy source.

It is to be understood that various changes and modifications may be made from the preferred embodiments discussed above without departing from the scope of the present invention, which is established by the following claims and equivalents thereof.

What is claimed is:

1. An orthodontic appliance, comprising:

a plastic orthodontic appliance having an appliance base and projecting structure extending outwardly from said appliance base, said projecting structure having an inner extremity integrally connected to said appliance base, an outer extremity, an intermediate section between said inner and outer extremities which has a lateral surface disposed generally orthogonally relative to said base and has a substantially uniform cross-section along substantially its entire length, thereby providing an intermediate section which is free of an increasing cross-sectional taper in a direction away from said appliance base, said projecting structure being fabricated substantially of plastic and free of one or more metal and/or ceramic structural reinforcing inserts, the cross-sectional area of said outer extremity being greater than the cross-sectional area of the intermediate section, thereby forming undercuts in said projecting structure to facilitate mechanically bonding said orthodontic appliance to a tooth surface with an adhesive.

2. The orthodontic appliance of claim 1 wherein said outer extremity of said projecting structure is oriented so as to conform to the curvature of a tooth.

3. The orthodontic appliance of claim 1 wherein said projecting structure is selected from the group consisting of a solid post or posts, a hollow tubular post or posts, a bristle or bristles, a ridge or ridges, and combinations thereof.

4. The orthodontic appliance of claim 1 wherein said projecting structure comprises a plurality of posts, each having an inner post extremity integrally connected to said appliance base, an outer post extremity, and a substantially nontapered intermediate post section between said inner and outer post extremities which has a lateral surface disposed generally orthogonally relative to said base and a substantially uniform cross-section along substantially its entire length, the cross-sectional area of said outer post extremity being greater than the cross-sectional area of the intermediate post section.

5. The orthodontic appliance of claim 4 wherein said posts are located on said appliance base at the intersection points of an imaginary grid.

6. The orthodontic appliance of claim 4 wherein each of said posts has a generally square-shaped cross-sectional area in said intermediate section.

7. The orthodontic appliance of claim 6 wherein said intermediate section has cross-sectional dimensionals of about 0.015 in. by about 0.015 in., and said posts are spaced at a center-to-center distance of approximately 0.030 in.

8. The orthodontic appliance of claim 7 wherein each of said posts has a length of from about 0.005 in. to about 0.010 in.

9. The orthodontic appliance of claim 1 wherein said appliance includes an archwire slot and a metal insert proximate said slot.

10. The orthodontic appliance of claim 1 wherein said plastic orthodontic appliance includes reinforcing glass fibers dispersed therein.

11. An orthodontic appliance, comprising:

a plurality of plastic orthodontic brackets, each bracket having an archwire slot, a bracket base and projecting structure extending outwardly from said bracket base, said projecting structure having an inner extremity integrally connected to said bracket base, an outer extremity and an intermediate section between said inner and outer extremities, the cross-sectional area of each of said outer extremities being greater than the cross-sectional area of the corresponding intermediate section, thereby forming undercuts in said projecting structure to facilitate mechanically bonding said orthodontic appliance to a tooth surface with an adhesive;

an adhesive disposed between a tooth surface and plurality of orthodontic brackets, including on said projecting structure and beneath the undercuts, for mechanically bonding said brackets to the teeth; and an archwire disposed within said archwire slots for transferring forces to the teeth.

12. The orthodontic appliance of claim 4 wherein said intermediate section has a cross-section area of about $2.25 \times 10^{-4}$ square inches.

13. The orthodontic appliance of claim 4 wherein said posts are spaced at a center-to-center distance of approximately 0.010 inches to about 0.020 inches.

14. The orthodontic appliance of claim 4 wherein each said post has a length of from about 0.005 inches to about 0.010 inches.

15. The orthodontic appliance of claim 14 wherein said intermediate section has a cross-sectional area of about $2.25 \times 10^{-4}$ square inches, and said posts are spaced at a center-to-center distance of approximately 0.010 inches to about 0.020 inches.

16. The orthodontic appliance of claim 1 wherein said outer extremity has a substantially distortion-free microstructure.

* * * * *